United States Patent [19]

Wakabayashi et al.

[11] Patent Number: 4,563,538

[45] Date of Patent: Jan. 7, 1986

[54] PROCESS FOR STABILIZING SILICON-CONTAINING METHACRYLATE

[75] Inventors: Hiroshi Wakabayashi; Takahisa Iwahara, both of Kobe, Japan

[73] Assignee: Kanegafuchi Kagaku Kogyo Kabushiki Kaisha, Osaka, Japan

[21] Appl. No.: 730,893

[22] Filed: May 6, 1985

[30] Foreign Application Priority Data

May 15, 1985 [JP] Japan .................................. 59-98056

[51] Int. Cl.[4] ........................... C07F 7/08; C07F 7/18; C07C 69/54
[52] U.S. Cl. ...................................... 556/401; 203/8; 203/62; 203/DIG. 21
[58] Field of Search .............................. 556/401; 203/8

[56] References Cited

U.S. PATENT DOCUMENTS 2,754,313 7/1956 Grubb .................................. 556/401
2,922,938 1/1960 Petley .............................. 556/401 X
3,801,615 4/1974 Chuang .............................. 556/401
3,816,267 6/1974 Chuang .......................... 556/401 X

FOREIGN PATENT DOCUMENTS 0736504 6/1966 Canada ................................. 556/401

Primary Examiner—Paul F. Shaver
Attorney, Agent, or Firm—Armstrong, Nikaido, Marmelstein & Kubovcik

[57] ABSTRACT

A process for stabilizing a silicon-containing methacrylate having the formula (I):

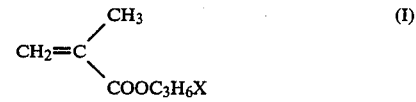

wherein X is $Si(OCH_3)_3$, $Si(OCH_3)_2CH_3$, $Si(OCH_3)(CH_3)_2$ or $Si(CH_3)_3$ which comprises adding 2,5-di-t-butylbenzoquinone to the silicon-containing methacrylate, whereby polymerization of the silicon-containing methacrylate can be inhibited. As a result, the silicon-containing methacrylate can be stabilized without any trouble in distillation step.

5 Claims, No Drawings

PROCESS FOR STABILIZING SILICON-CONTAINING METHACRYLATE

BACKGROUND OF THE INVENTION

The present invention relates to a process for stabilizing a silicon-containing methacrylate, and more particularly to a process for stabilizing a silicon-containing methacrylate having the formula (I):

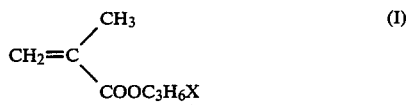

wherein X is $Si(OCH_3)_3$, $Si(OCH_3)_2CH_3$, $Si(OCH_3)(CH_3)_2$ or $Si(CH_3)_3$ which comprises adding 2,5-di-t-butylbenzoquinone to the silicon-containing methacrylate, whereby polymerization of the silicon-containing methacrylate can be inhibited.

In case that methacrylates are separated, concentrated or purified, distillation step is generally employed. However, it has been known that methacrylates have a property that methacrylates per se are very easy to polymerize, and particularly, the property is increased when methacrylates are treated at high temperature and are in vapor state as in distillation step. Therefore, a great attention must be given for inhibiting polymerization of methacrylates.

It has been recognized that the stability of a silicon-containing methacrylate represented by the formula (I), particularly methacryloyloxypropyltrimethoxysilane represented by the formula:

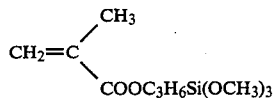

having a hydrolyzable silicone group such as trimethoxysilyl group and bonding to ester group, is the lowest among various known methacrylates. In case that the silicon-containing methacrylate having the formula (I) which has excellent polymerizable property is industrially prepared, it is very important that a trouble caused by polymerizing the silicon-containing methacrylate is inhibited in distillation step. Particularly, it is necessary and essential that the substantial inhibiting technique in polymerization of the silicon-containing methacrylate is established in order to operate continuously and stably in distillation step.

Examples of the polymerization inhibitor generally employed for methacrylates are, for instance, p-benzoquinone, hydroquinone, p-methoxyphenol, and the like. When methacrylates are distilled, however, the effect of stabilizing methacrylates is not so high as is expected in the above polymerization inhibitors. And further, when the silicon-containing methacrylate, particularly methacryloyloxypropyltrimethoxysilane is distilled, the above polymerization inhibitors are not industrially employed since the above polymerization inhibitor has substantially no effect of inhibiting polymerization of the silicon-containing methacrylate.

An object of the present invention is to provide a process for stabilizing the silicon-containing methacrylate having the formula (I) by adding the suitable polymerization inhibitor to the silicon-containing methacrylate, whereby polymerization of the silicon-containing methacrylate can be inhibited.

The present inventors have found a polymerization inhibitor having an excellent effect of inhibiting polymerization of the silicon-containing methacrylate having the formula (I), particularly methacryloyloxypropyltrimethoxysilane, in comparison with conventional polymerization inhibitors in distillation step.

SUMMARY OF THE INVENTION

In the present invention, there is provided a process for stabilizing the silicon-containing methacrylate having the formula (I):

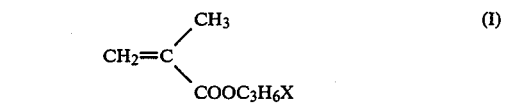

wherein X is $Si(OCH_3)_3$, $Si(OCH_3)_2CH_3$, $Si(OCH_3)(CH_3)_2$ or $Si(CH_3)_3$ which comprises adding 2,5-di-t-butylbenzoquinone to the silicon-containing methacrylate, whereby polymerization of the silicon-containing methacrylate can be inhibited.

DETAILED DESCRIPTION

Generally speaking, in case that methacrylates are distilled at high temperature and are in vapor state as in distillation step, a polymerization inhibitor upwardly passes through a distiller together with the desired methacrylates and exists in not less than amount for inhibiting polymerization of the distilled vapor methacrylates.

In the present invention, the silicon-containing methacrylate having the formula (I) can be stabilized and distilled without any trouble by employing the polymerization inhibitor which upwardly passes through a distiller together with the silicon-containing methacrylate and exists in not less than amount for inhibiting polymerization of the distilled vapor silicon-containing methacrylate in distillation step of the silicon-containing methacrylate.

That is, in the invention, the silicon-containing methacrylate having the formula (I) is stabilized by adding 2,5-di-t-butylbenzoquinone to the silicon-containing methacrylate, whereby polymerization of the silicon-containing methacrylate can be inhibited. Particularly, in case that the silicon-containing methacrylate is distilled for separating or purifying, the silicon-containing methacrylate is stabilized by means of the above method that polymerization of the silicon-containing methacrylate is inhibited.

An employed amount of 2,5-di-t-butylbenzoquinone must be determined depending upon kinds of the distillation, distillation time, maintenance of the distillation, distillation temperature, residence time of the silicon-containing methacrylate within a distiller, and the like. For instance, it is preferable that an amount of 2,5-di-t-butylbenzoquinone is 0.0001 to 1 part by weight against 100 parts by weight of vapor silicon-containing methacrylate upwardly passing through a distiller, more preferably 0.0005 to 0.1 part by weight.

In case that the silicon-containing methacrylate is distilled for purification, it is not necessary that 2,5-di-t-butylbenzoquinone must be supplied to the particular portion of a distiller and 2,5-di-t-butylbenzoquinone can be dissolved into a crude product having the silicon-containing methacrylate, particularly methacryloyloxypropyltrimethoxysilane.

The present invention is more specifically described and explained by means of the following Examples in which all parts are by weight unless otherwise noted. It is to be understood that the present invention is not limited to the Examples, and various changes and modifications may be made in the invention without departing from the spirit and scope thereof.

EXAMPLE 1

A marketed glass vacuum-distillation apparatus provided with a glass distiller having an inside diameter of 15 mm and a height of 150 mm, which is filled with glass Raschig rings of 3 mm, a thermometer, an eggplant flask, an adapter and two receptors was employed as an apparatus.

There was dissolved 0.08 g (800 ppm) of 2,5-di-t-butylbenzoquinone into 100 g of a crude mixture including methacryloyloxypropyltrimethoxysilane prepared by reacting methacryloyloxypropyltrichlorosilane and methanol as a main component (methacryloyloxypropyltrimethoxysilane content in the crude product measured by gas chromatography (hereinafter referred to as "GC") 94% by weight) and the apparatus was charged with the mixture. And then, the distillation of the mixture was carried out for 30 minutes in a vacuum while maintaining the distiller at 110° C. by means of an oil bath of 120° C. to give a fraction (I) and a fraction (II).

A weight proportion and a peak area ratio of the fractions and a crude mixture are shown in Table 1.

TABLE 1

|  | Weight proportion of fraction[1] | Peak area ratio[2] |
| --- | --- | --- |
| Fraction (I) | 5.4 | 0.11 |
| Fraction (II) | 85.2 | 0.10 |
| Crude mixture | — | 0.11 |

[1](Weight of fraction/weight of crude mixture before distillation) × 100
[2]Ratio of peak area of methacryloxypropyl-trimethoxy-silane and that of 2,5-di-t-butylbenzoquinone by means of GC. (The ratio is proportional to ratio of weight of 2,5-di-t-butylbenzoquinone.)

From the results, there are shown that an amount of 2,5-di-t-butylbenzoquinone does not scarcely change from the beginning of the distillation till a whole distillation ratio as is to 90.6%. From the results, it is further recognized that, in the distillation step, 2,5-di-t-butylbenzoquinone is upwardly passed through the distiller together with methacryloyloxypropyltrimethoxysilane vapor, and when 2,5-di-t-butylbenzoquinone vapor was cooled, a necessary amount of 2,5-di-t-butylbenzoquinone for inhibiting the polymerization of the distilled methacryloyloxypropyltrimethoxysilane vapor is collected.

EXAMPLE 2

Twenty mililiters test tube was charged with 5 g of crude mixture including methacryloyloxypropyltrimethoxysilane prepared by reacting methacryloyloxypropyltrichlorosilane and methanol (methacryloyloxypropyltrimethoxysilane content in the crude product measured by GC: 95% by weight) as a main component and 2.5 mg (500 ppm) of 2,5-di-t-butylbenzoquinone, and a condenser equipped with three-way-stop-cock was connected to the test tube. After the completion of predegasification (at 3 mmHg and for 20 minutes), the tube was dipped in an oil bath at 150° C. in a vacuum (3 mmHg). Water flowed through the condenser and the mixture was continued to heat for 20 hours under reflux. The mixture in the test tube did not lose any flowability and did not change into a gel. The obtained fraction included 93% by weight of methacryloyloxypropyltrimethoxysilane.

Comparative Example 1

The procedure in Example 1 was repeated except that 500 ppm of hydroquinone was employed instead of 2,5di-t-butylbenzoquinone. A viscosity of the mixture was increased and 7% by weight of the mixture changed into a gel in 3 hours.

Comparative Example 2

The procedure in Example 2 repeated except that 500 ppm of benzoquinone, p-methoxyphenol, copper (II) dimethyldithiocarbamate, nitrite or diphenylamine was employed instead of 2,5-di-t-butylbenzoquinone.

In all mixtures, a viscosity of the mixture was increased or the mixture changed into a gel.

EXAMPLE 3

A distillation apparatus provided with a distiller having an inside diameter of 200 mm and a length of 1,500 mm, the distiller being charged with 5 stainless network-fillers, having a height of 200 mm, a pipe for passing the fraction, a pipe for reflux, a pipe for supplying with the starting material and a still was installed so as to be able to perform continuously.

There was added 500 ppm of 2,5-di-t-butylbenzoquinone as a polymerization inhibitor to methacryloyloxypropyltrimethoxysilane and the apparatus was charged with the mixture. The mixture was continuously distilled by utilizing the apparatus.

When the distiller was disassembled after one month, it was recognized that methacryloyloxypropyltrimethoxysilane polymer was not produced.

Comparative Example 3

The procedure in Example 3 was repeated except that 500 ppm of p-methoxyphenol was employed as a polymerization inhibitor.

When the distiller was disassembled after 24 hours, it was recognized that methacryloyloxypropyltrimethoxysilane polymer adhered to the inside wall of the distiller.

What we claim is:

1. A process for stabilizing a silicon-containing methacrylate having the formula (I):

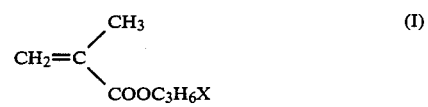

wherein X is $Si(OCH_3)_3$, $Si(OCH_3)_2CH_3$, $Si(OCH_3)(CH_3)_2$ or $Si(CH_3)_3$ which comprises adding 2,5-di-t-butylbenzoquinone to the silicon-containing methacrylate, whereby polymerization of the silicon-containing methacrylate can be inhibited.

2. The process for stabilizing of claim 1, wherein said silicon-containing methacrylate is that having the formula:

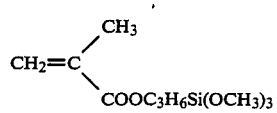

3. The process for stabilizing of claim 1, wherein an amount of said 2,5-di-t-butylbenzoquinone is 0.0001 part to 1 part by weight against 100 parts by weight of said silicon-containing methacrylate.

4. The process for stabilizing of claim 1, wherein an amount of said 2,5-di-t-butylbenzoquinone is 0.0005 part to 0.1 part by weight against 100 parts by weight of said silicon-containing methacrylate.

5. In a process for distilling a silicon-containing methacrylate having the formula (I):

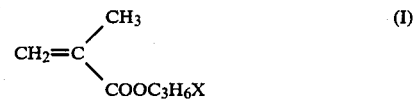

wherein X is $Si(OCH_3)_3$, $Si(OCH_3)_2CH_3$, $Si(OCH_3)(CH_3)_2$ or $Si(CH_3)_3$ from a crude product including the silicon-containing methacrylate for purification, the improvement which comprises adding 2,5-di-t-butylbenzoquinone to the crude product.

* * * * *